US011604060B2

(12) United States Patent
Eggleston et al.

(10) Patent No.: US 11,604,060 B2
(45) Date of Patent: Mar. 14, 2023

(54) APPARATUS FOR OPTICAL COHERENCE TOMOGRAPHY

(71) Applicant: Nokia Technologies Oy, Espoo (FI)

(72) Inventors: Michael Eggleston, Columbus, OH (US); Mark Earnshaw, Berkeley Heights, NJ (US); Cristian Bolle, Murray Hill, NJ (US); Flavio Pardo, Glen Gardner, NJ (US)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 16/969,021

(22) PCT Filed: Feb. 20, 2019

(86) PCT No.: PCT/FI2019/050133
§ 371 (c)(1),
(2) Date: Aug. 11, 2020

(87) PCT Pub. No.: WO2019/162571
PCT Pub. Date: Aug. 29, 2019

(65) Prior Publication Data
US 2021/0025691 A1    Jan. 28, 2021

(30) Foreign Application Priority Data
Feb. 26, 2018  (EP) ..................................... 18158662

(51) Int. Cl.
*G01B 9/02*    (2022.01)
*G01B 9/02091*    (2022.01)
*A61B 5/00*    (2006.01)

(52) U.S. Cl.
CPC ........ *G01B 9/02091* (2013.01); *A61B 5/0066* (2013.01); *A61B 5/6823* (2013.01); *G01B 9/02034* (2013.01)

(58) Field of Classification Search
CPC ............ G01B 9/02091; G01B 9/02034; G01B 2290/65; A61B 5/0066; A61B 5/6801; A61B 5/6823
See application file for complete search history.

(56) References Cited

U.S. PATENT DOCUMENTS 7,468,997 B2    12/2008  Jayaraman
2009/0284749 A1*  11/2009  Johnson ............. G01B 9/02057
                                                        356/497

(Continued)

OTHER PUBLICATIONS

Dynamic focus control in high-speed optical coherence tomography based on a microelectromechanical mirror, Optics Communications 232 (2004) pp. 123-128, Qi et al (Year: 2004).*

(Continued)

*Primary Examiner* — Tarifur R Chowdhury
*Assistant Examiner* — Jonathon Cook
(74) *Attorney, Agent, or Firm* — Harrington & Smith

(57) ABSTRACT

Examples of the disclosure relate to an apparatus (101), a wearable electronic device and an optical arrangement for optical coherence tomography. The apparatus comprises an optical coherence tomography system (103) and an optical arrangement (105). The optical arrangement comprises at least one means for beam shaping (109) configured to shape a beam of light from the optical coherence tomography system. The optical arrangement also comprises at least one mirror (111) positioned so that light from the means for beam shaping is incident on the at least one mirror. The at least one mirror is configured to move in at least one direction relative to the optical coherence tomography system.

16 Claims, 7 Drawing Sheets

(56) References Cited

U.S. PATENT DOCUMENTS

| | | | |
|---|---|---|---|
| 2010/0049002 A1 | 2/2010 | Feldman et al. | |
| 2011/0130652 A1* | 6/2011 | Boppart | A61B 3/102 600/425 |
| 2011/0222020 A1* | 9/2011 | Izatt | G01B 9/02091 351/205 |
| 2011/0299096 A1 | 12/2011 | Knobbe | |
| 2014/0176958 A1 | 6/2014 | Flanders et al. | |
| 2014/0276014 A1* | 9/2014 | Khanicheh | A61B 5/4064 600/425 |
| 2014/0354950 A1 | 12/2014 | Buckland et al. | |
| 2015/0366451 A1* | 12/2015 | Liu | A61B 3/0008 356/456 |
| 2016/0109699 A1* | 4/2016 | Margallo | G02B 6/12004 359/201.2 |
| 2016/0238371 A1 | 8/2016 | Lloret Soler et al. | |
| 2017/0017083 A1 | 1/2017 | Samec et al. | 27/172 |
| 2017/0100064 A1 | 4/2017 | Van Dorpe et al. | |
| 2017/0314763 A1 | 11/2017 | Petronius et al. | |

OTHER PUBLICATIONS

Yurtsever, Günay & Weiss, Nicolas & Kalkman, J. & van Leeuwen, Ton & Baets, Roel. (2014), Ultra-compact silicon photonic integrated interferometer for swept-source optical coherence tomography, Optics Letters. 39, 10.1364/OL.39.005228 (Year: 2014).*

M. Brandl, Thin Spherical lenses, Nov. 26, 2022, http://www.physnet.org/modules/pdf_modules/m223.pdf (Year: 2002).*

Schneider et al., "Optical Coherence Tomography System Mass-producible on a Silicon Photonic Chip", Optics Express, vol. 24, No. 2, Jan. 2016, pp. 1573-1586.

Heck, "Highly Integrated Optical Phased Arrays: Photonic Integrated Circuits for Optical Beam Shaping and Beam Steering", Nanophotonics, vol. 6, No. 1, 2017, pp. 93-107.

Wang et al., "Silicon Photonic Integrated Circuit Swept-source Optical Coherence Tomography Receiver with Dual Polarization, Dual Balanced, In-phase and Quadrature Detection", Biomedical Optics Express, vol. 6, No. 7, Jun. 2015, pp. 2562-2574.

Akca et al., "Towards a Miniaturized Optical Coherence Tomography System", CLEO: Laser Science to Photonic Applications, 2011, 2 pages.

Strathman et al., "MEMS Scanning Micromirror for Optical Coherence Tomography", Biomedical Optics Express, vol. 6, No. 1, Dec. 2014, pp. 211-224.

Duan et al., "Optical Coherence Tomography Endoscopic Probe Based on a Tilted Mems Mirror", Biomedical Optics Express, vol. 7, No. 9, Sep. 2016, pp. 3345-3354.

Extended European Search Report received for corresponding European Patent Application No. 18158662.9, dated Oct. 10, 2018, 7 pages.

International Search Report and Written Opinion received for corresponding Patent Cooperation Treaty Application No. PCT/FI2019/050133, dated Jun. 14, 2019, 11 pages.

Wijesinghe, Ruchire Eranga, et al., "Optical coherence tomography—integrated, wearable (backpack-type), compact diagnostic imaging modality for in situ leaf quality assessment", Applied Optics, vol. 56, No. 9, Mar. 20, 2017, 7 pages.

* cited by examiner

APPARATUS FOR OPTICAL COHERENCE TOMOGRAPHY

RELATED APPLICATION

This application claims priority to PCT Application No. PCT/FI2019/050133, filed on Feb. 20, 2019, which claims priority to European Application No. 18158662.9, filed on Feb. 26, 2018, each of which is incorporated herein by reference in its entirety.

TECHNOLOGICAL FIELD

Examples of the disclosure relate to apparatus for optical coherence tomography. The apparatus could be used in wearable devices.

BACKGROUND

Optical coherence tomography enables cross sectional imaging of an object by detecting light reflected from internal structures within the object. Optical coherence tomography can be used to image biological tissues of a subject such as a retina, teeth, skin or other suitable parts of a subject. Optical coherence tomography can therefore provide useful information that can be used to assist in diagnosis of medical conditions.

BRIEF SUMMARY

According to various, but not necessarily all, examples of the disclosure there is provided an apparatus comprising: an optical coherence tomography system; and an optical arrangement wherein the optical arrangement comprises at least one means for beam shaping configured to shape a beam of light from the optical coherence tomography system and at least one mirror positioned so that light from the means for beam shaping is incident on the at least one mirror and wherein the at least one mirror is configured to move in at least one direction relative to the optical coherence tomography system.

The optical arrangement and the optical coherence tomography system may be, at least in part, mounted on a substrate.

The optical coherence tomography system may comprise an integrated optoelectronic circuit comprising at least an interferometer configured for optical coherence tomography.

The at least one mirror may comprise a micro-electromechanical mirror.

The optical arrangement may comprise a first mirror configured to move in a first direction and also a second direction wherein the first direction is different to the second direction.

The optical arrangement may comprise a first mirror configured to move in a first direction and a second mirror configured to move in a second direction wherein the first direction is different to the second direction.

The second direction may be perpendicular to the first direction.

The at least one mirror may be provided on a substrate and the substrate may be provided at an incline relative to the optical coherence tomography system.

The at least one mirror may be provided on a substrate and the mirror may be provided at an incline relative to the substrate.

The angle of incline may be 45 degrees.

The means for beam shaping may comprise means for collimating light.

The means for beam shaping may comprise at least one spherical lens.

According to various, but not necessarily all, examples of the disclosure there is provided a wearable electronic device comprising an apparatus as described above and means for attaching the optical coherence tomography device to a subject.

The means for attaching the apparatus to a subject may comprise a strap.

According to various, but not necessarily all, examples of the disclosure there is provided an optical arrangement comprising: at least one means for beam shaping configured to shape a beam of light from an optical coherence tomography system; and at least one mirror positioned so that light from the means for beam shaping is incident on the at least one mirror and wherein the at least one mirror is configured to move in at least one direction relative to the optical coherence tomography system.

According to various, but not necessarily all, examples of the disclosure there is provided a method comprising: providing an optical coherence tomography system; and positioning an optical arrangement relative to the optical coherence tomography system so that light from the optical coherence tomography system is incident on the optical arrangement, wherein the optical arrangement comprises at least one means for beam shaping configured to shape a beam of light from the optical coherence tomography system and at least one mirror positioned so that light from the means for beam shaping is incident on the at least one mirror and wherein the at least one mirror is configured to move in at least one direction relative to the optical coherence tomography system.

According to various, but not necessarily all, examples of the disclosure there is provided an apparatus comprising: an optical coherence tomography system; and an optical arrangement wherein the optical arrangement comprises at least one beam shaper configured to shape a beam of light from the optical coherence tomography system and at least one mirror positioned so that light from the beam shaper is incident on the at least one mirror and wherein the at least one mirror is configured to move in at least one direction relative to the optical coherence tomography system.

The beam shaper may be configured to collimate a beam of light.

The beam shaper may comprise at least one spherical lens.

According to various, but not necessarily all, examples of the disclosure there is provided a wearable electronic device comprising an apparatus as described above and at least one attachment portion configured to attach the optical coherence tomography device to a subject.

The at least one attachment portion may comprise a strap.

According to various, but not necessarily all, examples of the disclosure there is provided an optical arrangement comprising: at least one beam shaper configured to shape a beam of light from an optical coherence tomography system; and at least one mirror positioned so that light from the beam shaper is incident on the at least one mirror and wherein the at least one mirror is configured to move in at least one direction relative to the optical coherence tomography system.

According to various, but not necessarily all, examples of the disclosure there is provided a method comprising: providing an optical coherence tomography system; and positioning an optical arrangement relative to the optical coherence tomography system so that light from the optical coherence tomography system is incident on the optical arrangement, wherein the optical arrangement comprises at least one beam shaper configured to shape a beam of light from the optical coherence tomography system and at least one mirror positioned so that light from the beam shaper is incident on the at least one mirror and wherein the at least one mirror is configured to move in at least one direction relative to the optical coherence tomography system.

BRIEF DESCRIPTION

For a better understanding of various examples that are useful for understanding the detailed description, reference will now be made by way of example only to the accompanying drawings in which:

FIG. 1 schematically illustrates an example apparatus;

DETAILED DESCRIPTION

Examples of the disclosure relate to an apparatus 101 for optical coherence tomography. The apparatus 101 comprises an optical coherence tomography system 103. The optical coherence tomography system 103 may comprise an interferometer and other components that may enable light to be provided to a sample and reflected light to be analysed to obtain an optical coherence tomography image. The apparatus 101 also comprises an optical arrangement 105. The optical arrangement 105 may be coupled to the optical coherence tomography system 103 so that light from the optical coherence tomography system 103 is incident on the optical arrangement 105. The optical arrangement 105 is configured to enable the light to be scanned in at least one direction to enable a multi-dimensional optical coherence tomography image to be obtained. The optical coherence tomography system 103 and the optical arrangement 105 are small enough to be provided in a wearable device.

Figure 1:
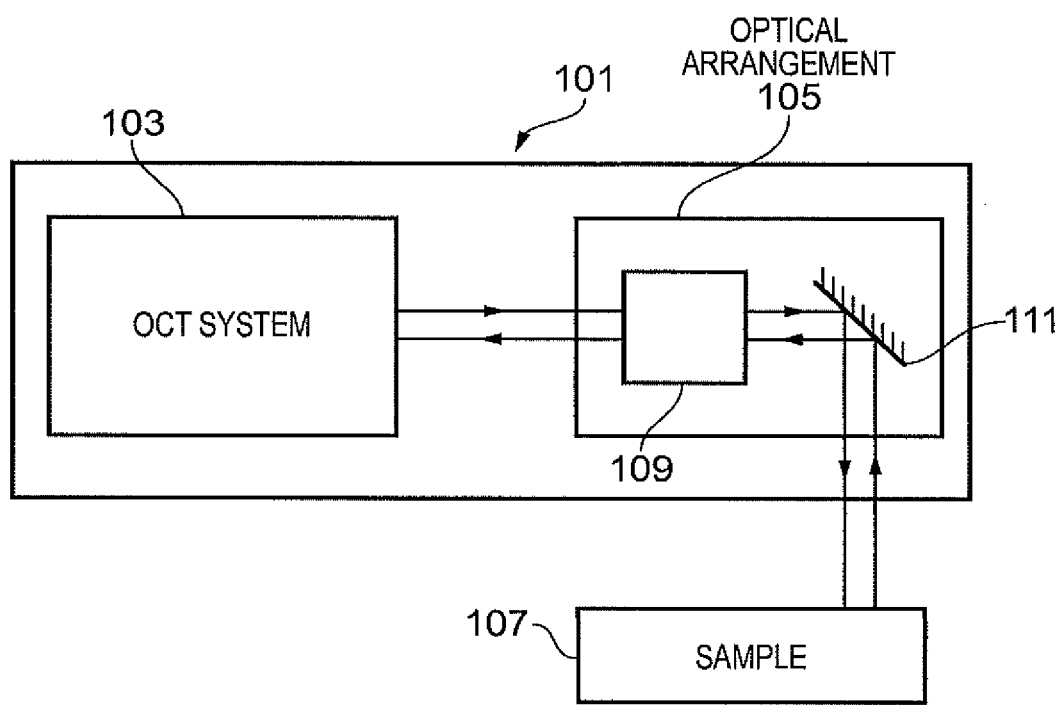

FIG. 1 schematically illustrates an apparatus 101 according to examples of the disclosure. The apparatus 101 comprises an optical coherence tomography system 103 and an optical arrangement 105. It is to be appreciated that in examples of the disclosure the apparatus 101 may comprise additional components that are not shown in FIG. 1. For example, one or more lenses or other optical components may be provided to focus the light as needed.

The optical coherence tomography system 103 comprises means for providing a beam of light to a sample 107 and means for receiving reflected light back from the sample 107. The optical coherence tomography system 103 may also comprise means for combining the reflected light with reference light to enable the interference between the reflected light and the reference light to be analysed. For example, the optical coherence tomography system 103 may comprise an interferometer and any other suitable means.

Figure 9:
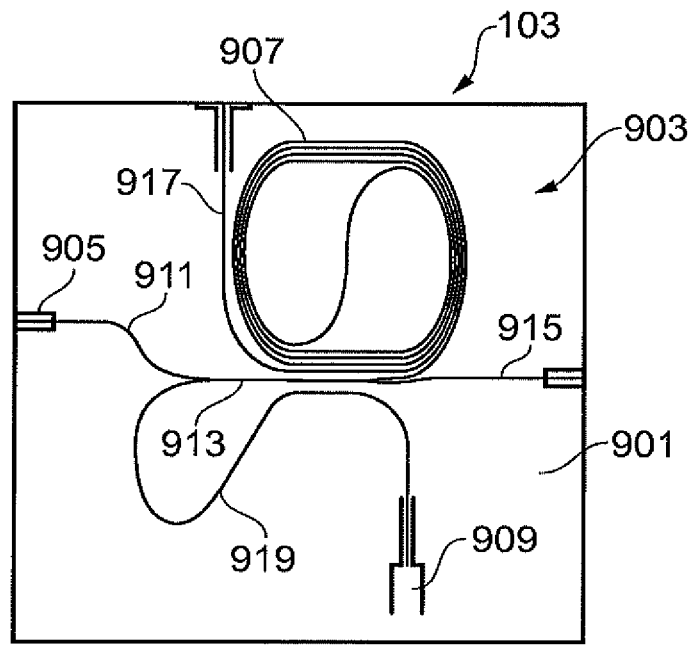
FIG. 9 illustrates an example integrated optoelectronic circuit which may be used in some examples of the disclosure.

In some examples the optical coherence tomography system 103 may comprise an integrated optoelectronic circuit. The integrated optoelectronic circuit may comprise an interferometer which may be configured for optical coherence tomography. In some examples the integrated optoelectronic circuit may also comprise additional components such as a light source and one or more detectors. FIG. 9 illustrates an example optoelectronic circuit which may be used in some examples of the disclosure.

The optical arrangement 105 is positioned within the apparatus 101 so that light from the optical coherence tomography system 103 is incident on the optical arrangement 105. The optical arrangement 105 comprises means for beam shaping 109 and at least one mirror 111. It is to be appreciated that the optical arrangement 105 could comprise additional components.

The means for beam shaping 109 may comprise any means which may be configured to shape a beam of light from the optical coherence tomography system 103. In some examples the means for beam shaping 109 could comprise means for collimating light or any other suitable means. The means for collimating light could comprise any means for providing a beam of light with parallel rays, or substantially parallel rays. The means for beam shaping 109 may be configured to reduce the divergence of the beam of light from the optical coherence tomography system 103. In some examples the means for beam shaping 109 may be configured to minimise the divergence of the beam of light from the optical coherence tomography system 103.

The means for beam shaping 109 could comprise a spherical lens or any other suitable means.

The means for beam shaping 109 is positioned within the apparatus 101 so that it is located between the optical coherence tomography system 103 and the mirror 111. In examples of the disclosure light from the optical coherence tomography system 103 passes through the means for beam shaping 109 before it is incident on the mirror 111.

The at least one mirror 111 comprises any means which may be configured to reflect a beam of light. In some examples the mirror 111 may be completely reflective so that all, or substantially all, of the light that is incident on the mirror 111 is reflected.

The at least one mirror 111 may comprise any suitable type of mirror. In some examples the at least one mirror 111 may comprise a micro-electromechanical (MEM) mirror or any other suitable type of mirror 111.

In the example of FIG. 1 the mirror 111 is a planar, or substantially planar mirror. In other examples the mirror 111 could have a different shape. For example the mirror 111 could be a curved mirror.

The at least one mirror 111 is configured so that light from the means for beam shaping 109 is incident on the mirror 111. The at least one mirror 111 is configured so that the light is reflected from the mirror 111 towards the sample 107. The at least one mirror 111 is also configured so that at least some of the light reflected back from the sample 107 is incident on the mirror 111. The light reflected back from the sample 107 is then reflected by the mirror 111 back though the means for beam shaping 109 and back into the optical coherence tomography system 103. This enables the light reflected back from the sample 107 to be combined with reference light by the optical coherence tomography system 103.

The at least one mirror 111 may be configured to move in at least one direction relative to the optical coherence tomography system 103. In some examples the mirror 111 may move relative to the means for beam shaping 109. In other examples the optical arrangement 105 could be configured so that both the mirror 111 and the means for beam shaping 109 can be moved relative to the optical coherence tomography system 103.

In the example of FIG. 1 the optical arrangement 105 comprises a single mirror 111. The single mirror 111 may be configured to move in a first direction and also a second direction.

The first direction could be perpendicular, or substantially perpendicular, to the second direction. For example the first direction could correspond to and x axis while the second direction could correspond to a y axis. This may enable the beam of light from the optical coherence tomography system 103 to be scanned in two dimensions so that images can be obtained for different areas of the sample 107. This may enable a three dimensional optical coherence tomography image to be obtained.

In other examples the optical arrangement 105 could comprise two or more mirrors 111. In such examples a first mirror 111 could be configured to be moved in the first direction and a second mirror 111 could be configured to be moved in the second direction. This could be provided as an alternative to having a single mirror 111 configured to move in two different dimensions.

In other examples the mirror 111 may have additional degrees of freedom. For example, the position of the mirror could be adjusted to provide tuneable focus or any other suitable means.

The sample 107 that is imaged by the apparatus 1 could comprise any suitable object. In some examples the sample 107 could comprise biological tissue of a subject. In some examples the sample 107 could comprise a subject's retina, teeth, skin or any other suitable body part. Different apparatus 101 could be configured to image different types of samples 107.

Figure 2:
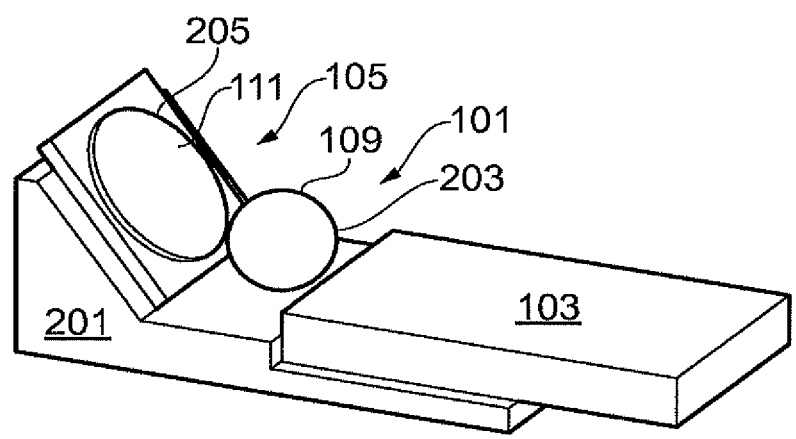
FIG. 2 illustrates an apparatus.

FIG. 2 illustrates an example apparatus 101. In the example of FIG. 2 the apparatus 1 comprises an optical coherence tomography system 103, an optical arrangement 105 and a substrate 201. The optical arrangement 105 comprises a means for beam shaping 109 and a mirror 111.

In the example of FIG. 2 the means for beam shaping 109 comprises a spherical lens 203 and the mirror 111 comprises a MEM mirror 205. Other types of means for beam shaping 109 and/or mirrors 111 could be used in other examples of the disclosure.

The substrate 201 may provide supporting means for the components of the apparatus 101. The components of the apparatus 101 may be mounted on the substrate 201. This enables the optical coherence tomography system 103 and the optical arrangement 105 to be provided on the same substrate 201.

In some examples the apparatus 101 may be configured so that all of the components of the apparatus 101 are fully mounted on the substrate 201. In some examples the apparatus 101 may be configured so that some of the components of the apparatus 101 are only partially mounted on the substrate 201.

The substrate 201 may comprise any suitable material. In some examples the substrate 201 may comprise silicon.

In the example of FIG. 2 the substrate 201 has a stepped surface so that different parts of the surface of the substrate 201 are provided at different levels. In the examples of FIG. 2 this enables the optical coherence tomography system 103 to be provided at a first level and the means for beam shaping 109 is provided at a second level where the first level is different to the second level.

In the example of FIG. 2 the substrate 201 also has an inclined portion. The mirror 111 is provided on the inclined portion of the substrate 201. The inclined portion of the substrate 201 is inclined relative to the optical coherence tomography system 103 and the portion of the substrate 201 on which the optical coherence tomography system 103 is mounted.

The mirror 111 is mounted so that is it parallel to the inclined portion of the substrate 201. This enables the mirror 111 to be provided at an inclined angle relative to the optical coherence tomography system 103 and/or other components of the apparatus 101.

In the example of FIG. 2 the inclined portion of the substrate 201 has an angle of incline of 45 degrees, or substantially 45 degrees. Other optical arrangements 105 may have different configurations for the mirrors 111 and their relative angles.

Figure 3:
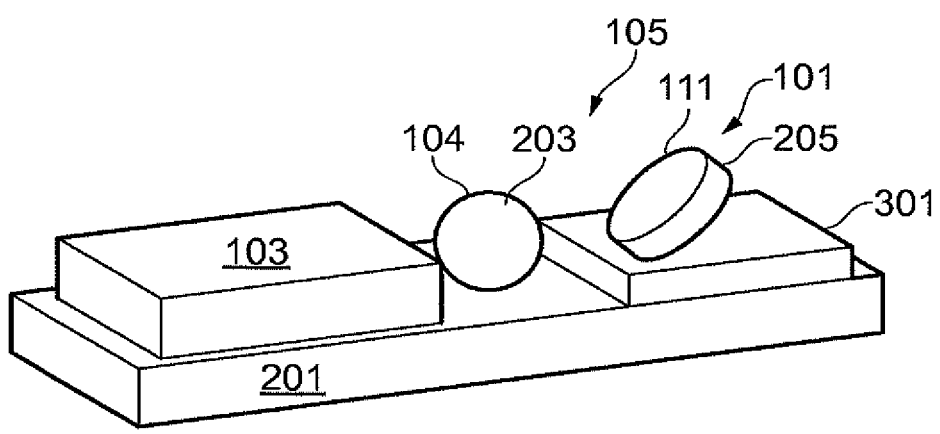
FIG. 3 illustrates another example apparatus.

FIG. 3 illustrates another example apparatus 101. In the example of FIG. 3 the apparatus 1 also comprises an optical coherence tomography system 103, an optical arrangement 105 and a substrate 201. The optical arrangement 105 also comprises a means for beam shaping 109 and a mirror 111.

In the example of FIG. 3 the means for beam shaping 109 comprises a spherical lens 203 and the mirror 111 comprises a MEM mirror 205. Other types of means for beam shaping 109 and/or mirrors 111 could be used in other examples of the disclosure.

In the example of FIG. 3 the substrate 201 also provide supporting means for the components of the apparatus 101 so that the components of the apparatus 101 may be mounted on the substrate 201. This enables the optical coherence tomography system 103 and the optical arrangement 105 to be provided on the same substrate 201.

The substrate 201 used in the example of FIG. 3 may comprise any suitable material. In some examples the substrate 201 may comprise silicon.

In the example of FIG. 3 the substrate 201 has a flat, or substantially flat, surface. The surface of the substrate 201 may be flat so that the respective components of the apparatus 101 are provided at the same level, or substantially the same level. For example, in FIG. 3 the optical coherence tomography system 103 and the means for beam shaping 109 are provided at the same level.

In the example of FIG. 3 the mirror 111 is provided on a support 301. The support 301 could comprise a secondary substrate which is smaller than the substrate 201 on which the other components of the apparatus 101 are provided. The support 301 is mounted on the flat surface of the substrate 201.

The mirror 111 is mounted on the support 301 so that it is provided at an inclined angle to the support 301. This enables the mirror 111 to be provided at an inclined angle relative to the optical coherence tomography system 103 and/or other components of the apparatus 101.

In the example of FIG. 3 the inclined portion of the substrate 201 has an angle of incline of 45 degrees, or substantially 45 degrees. Other optical arrangements 105 may have different configurations for the mirrors 111 and their relative angles.

Figure 4:
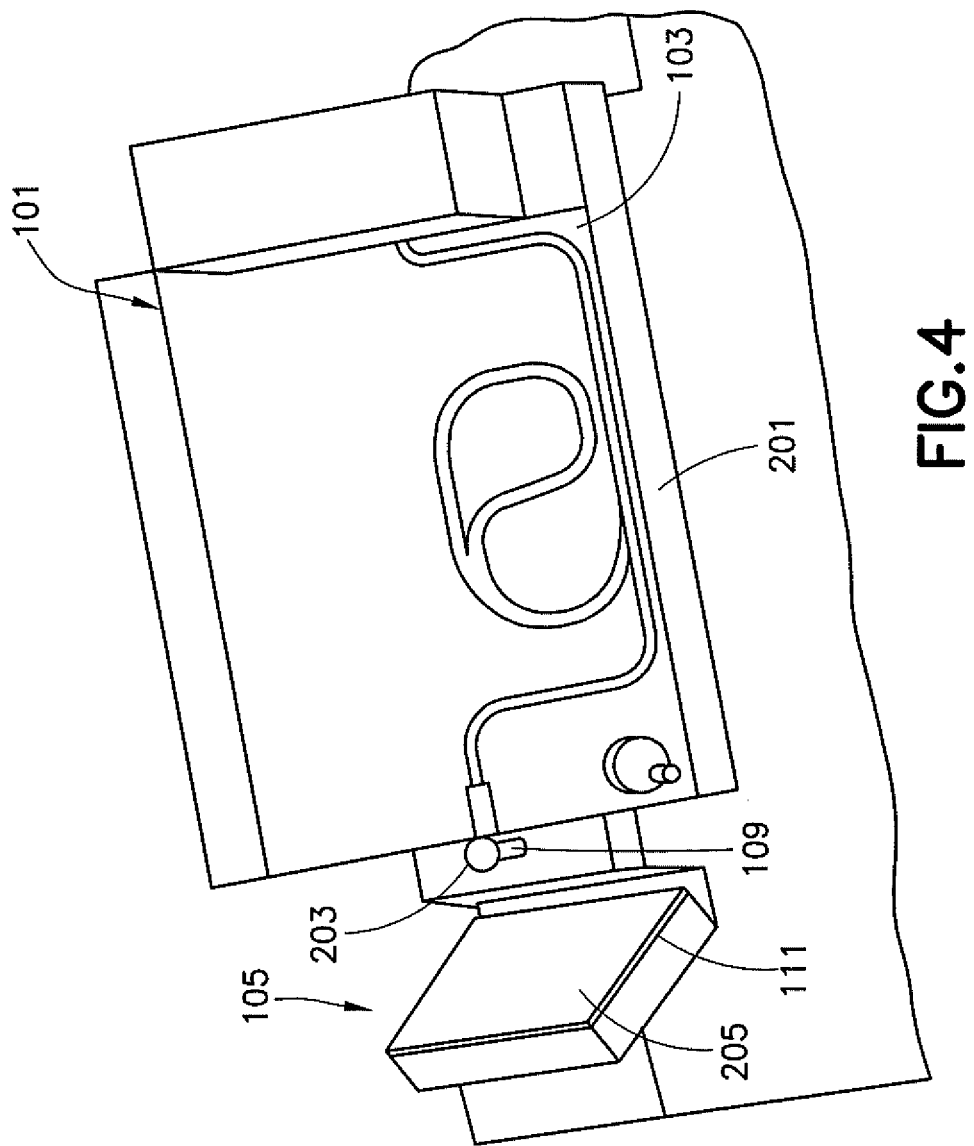
FIG. 4 is a photograph of an example apparatus.

FIG. 4 is a photograph of an example apparatus 101. The example apparatus 101 in FIG. 4 has a configuration similar to the configuration shown in FIG. 2.

The apparatus 101 comprises a substrate 201 with a stepped surface. The optical coherence tomography system 103 is provided at a first level on the stepped surface of the substrate 201 and the means for beam shaping 109 is provided at a second level on the stepped surface of the substrate 201. The second level has a different height relative to the first level.

In the example of FIG. 4 the optical coherence tomography system 103 comprises an integrated optoelectronic circuit. The integrated optoelectronic circuit may be small enough to enable the apparatus 101 to be used within a wearable device and/or to be used as a portable device.

The means for beam shaping 109 comprises a spherical lens 203. The spherical lens 203 is provided adjacent to a light guide of the integrated optoelectronic circuit so that light from the optical coherence tomography system 103 passes through the spherical lens 203.

The mirror 111 comprises a MEM mirror 205 which is mounted on an inclined portion of the substrate 201 so that the mirror 111 is inclined at an angle of 45 degrees, or substantially 45 degrees, to the optical coherence tomography system 103.

Figure 5:
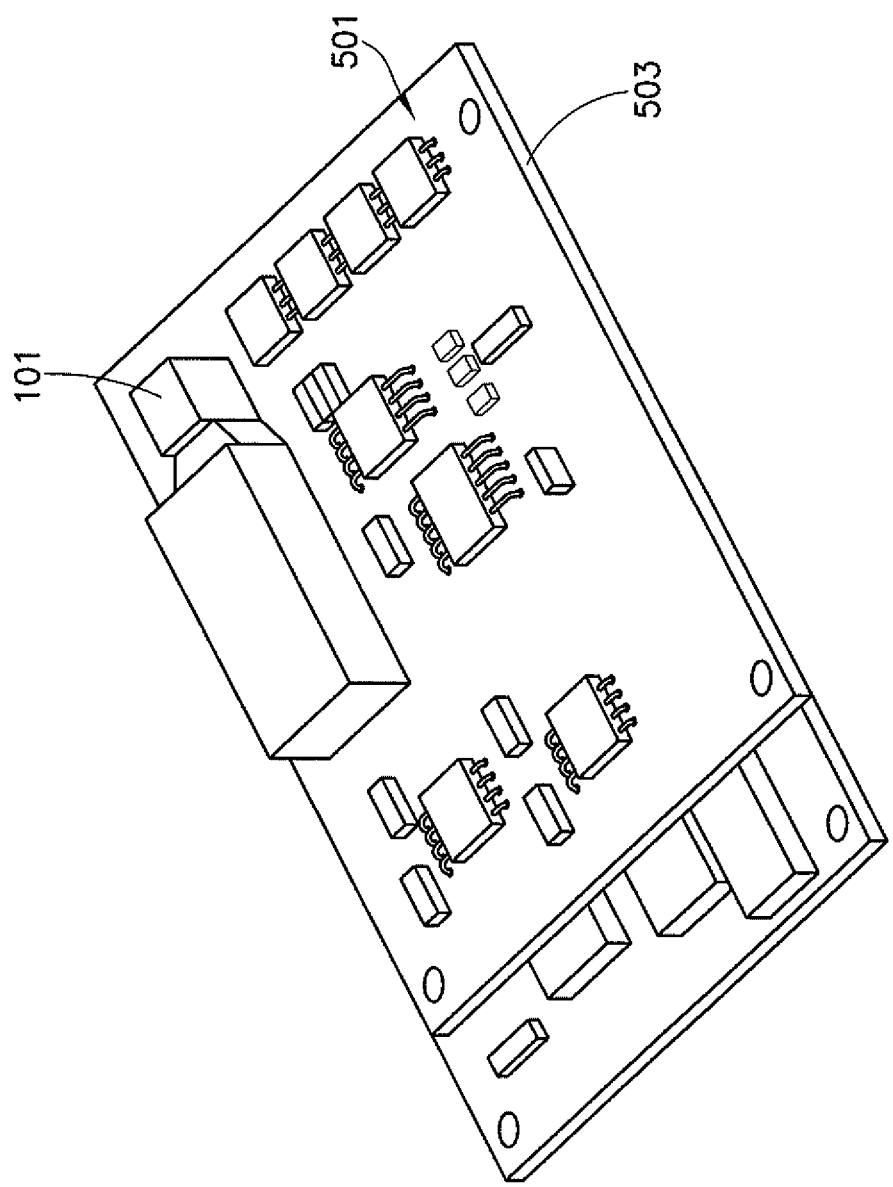
FIG. 5 is photograph of an optical coherence tomography device comprising an example apparatus.

FIG. 5 is photograph of an optical coherence tomography device 501 comprising an example apparatus 101. The example apparatus 101 could be the apparatus 101 shown in FIG. 4 or any other suitable apparatus 101.

The example optical coherence tomography device 501 also comprises circuitry 503. The circuitry 503 could be controlling circuitry which may comprise processing circuitry and memory circuitry. The circuitry 503 may be configured to obtain an output from the optical coherence tomography system 103 and process the output to provide image data. The circuitry 503 could comprise means for processing an output from the optical coherence tomography system 103 to provide image data. The image data could be used to provide a three dimensional optical coherence tomography image. The image data could be provided to a display or other image rendering device to enable the image data to be rendered into an image.

Figure 6:
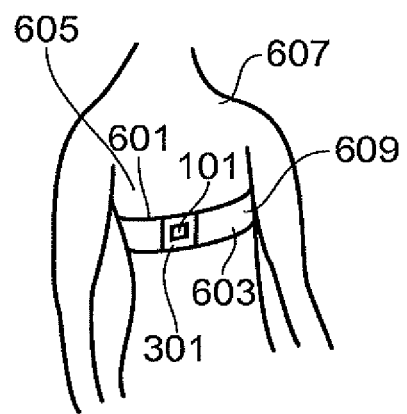
FIG. 6 illustrates an example of a wearable electronic device comprising an example apparatus.

FIG. 6 illustrates an example wearable electronic device 601 according to examples of the disclosure. The wearable electronic device 601 comprises an apparatus 101 and means 603 for attaching the apparatus 101 to a subject. In the example of FIG. 6 the wearable electronic device 601 is shown attached to the torso 605 of a subject 607.

The apparatus 101 which is used within the wearable electronic device 601 may be as described above or may be any other suitable apparatus 101. For example, the apparatus 101 could be any of the apparatus 101 shown in FIGS. 1 to 4 or a different apparatus 101. In some examples the apparatus 101 may be provided within an optical coherence tomography device 501 which could be as shown in FIG. 5.

The means 603 for attaching the apparatus 101 to a subject 607 may comprise any means which enables the apparatus 101 to be secured to the body of a subject 607 so that the apparatus 101 can obtain images of a part of the body of the subject 607.

In the example of FIG. 6 the means 603 for attaching the apparatus 101 to a subject 607 comprises a strap 609. The strap 609 may be sized and shaped to fit around any suitable part of the subject 607. In the example of FIG. 6 the strap 609 is configured to fit around the torso 605 of the subject 607. This may enable the subject's chest or other part of their torso 605 to be analysed using the apparatus 101.

In other examples the strap 609 could be sized and shaped to fit around a different part of the subject 607. For instance, in some examples the strap 609 could be sized and shaped to fit around the subject's arm. In such examples the apparatus 101 could be integrated within a watch or other wrist mounted device.

In other examples the apparatus 101 could be configured to obtain images of a subject's retina or other part of their eye. In such examples the apparatus 101 could be integrated within a head mounted device or any other suitable wearable device.

In other examples the wearable electronic device 601 and the apparatus 101 could be configured to be attached to a different part of a subject. For example the wearable electronic device 601 and the apparatus 101 could be configured to fit to a subject's finger, ear lobe or any other suitable part of their body.

In the example of FIG. 6 the wearable electronic device 601 comprises a single apparatus 101. In other examples the wearable electronic device could comprise a plurality of apparatus 101. In such examples the wearable electronic device 601 may be configured so that different apparatus 101 can obtain images of different parts of the subject.

Figure 7:
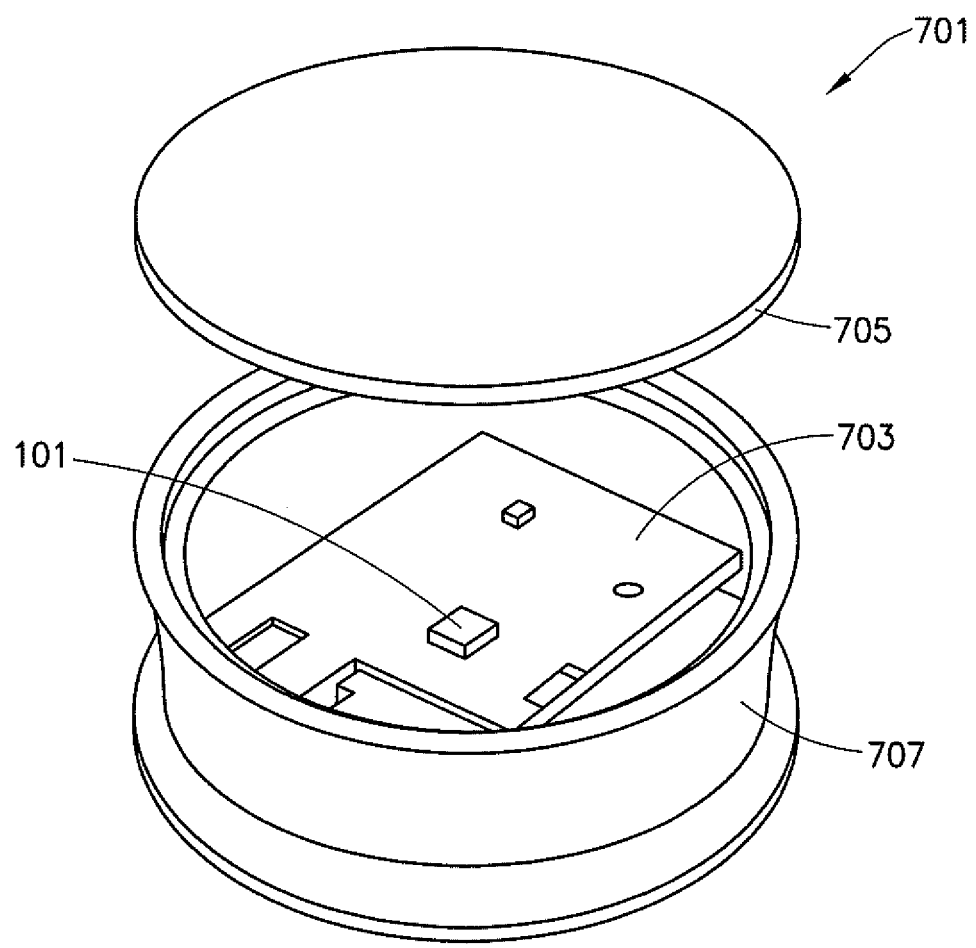
FIG. 7 illustrates a portable electronic device comprising an example apparatus.

FIG. 7 illustrates a portable electronic device 701 comprising an example apparatus 101.

In the example of FIG. 7 the apparatus 101 is provided on a circuit board 703. Additional components of the portable electronic device 701 may also be provided on the circuit board 703. For instance, in some examples of the disclosure circuitry 503 may be provided on the circuit board 703.

The apparatus 101 and the circuit board 703 are provided within a casing 707. The casing 707 comprises a lid 705. The lid 705 and casing 707 are shown in an exploded view in FIG. 7. It is to be appreciated that in examples of the disclosure the lid 705 could be secured to the rest of the casing 707.

The apparatus 101 may be provided within the casing 707 so that light can be provided from the apparatus 101 to a sample 107 and so that light reflected back from the sample 107 can be received by the apparatus 101. In some examples the casing 707 may comprise a portion which is transparent, or at least partially transparent, to the light provided by the apparatus 101.

The portable electronic device 701 may be small enough so that it can be easily transported by a subject. In some examples the portable electronic device 701 may be small enough so that it can be held in the hand of a subject. In some examples of the disclosure, the portable electronic device 701 may have a diameter of 5 cm or less. This may enable the portable electronic device 701 to be transported by a subject and may also enable the portable electronic device 701 to be provided within a wearable electronic device 601. The portable electronic device may have different size and/or shape in other examples of the disclosure.

Figure 8:
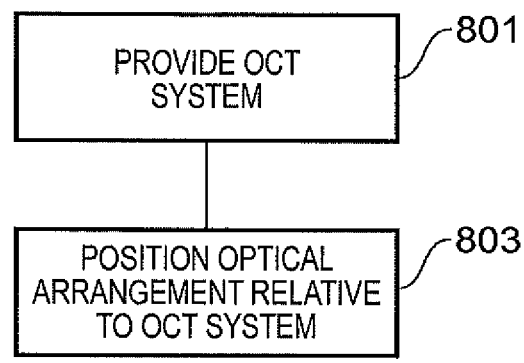
FIG. 8 illustrates an example method of forming an apparatus.

FIG. 8 illustrates an example method of forming an apparatus 101. The method may be used to form an apparatus 101 which may be as described above.

The method comprises, at block 801, providing an optical coherence tomography system 103. The optical coherence tomography system 103 could comprise an integrated optoelectronic circuit as shown in FIG. 9, or any other suitable components.

At block 803 the method comprises positioning an optical arrangement 105 relative to the optical coherence tomography system 103 so that light from the optical coherence tomography system is incident on the optical arrangement 105. The optical arrangement 105 may comprise at least one means for beam shaping 109. The means for beam shaping 109 are configured to shape a beam of light from the optical coherence tomography system 103. The optical arrangement also comprises at least one mirror 111 positioned so that light from the means for beam shaping 109 is incident on the at least one mirror 111. The least one mirror 111 is also configured to move in at least one direction relative to the at least one means for beam shaping 109.

In some examples the optical arrangement 105 may be provided independently of the optical coherence tomography system 103. For examples the optical arrangement 105 could be formed on the substrate 201 and then the optical coherence tomography system 103 could be added to the substrate 201.

It is to be appreciated that in some examples the method may comprise additional blocks that are not shown in FIG. 8. For example, the method could comprise providing one or more additional optical components within the optical arrangement 105.

Once the apparatus 101 has been formed the apparatus 101 may be coupled to one or more additional components to provide an optical coherence tomography device 501. For example, the method could comprise additional blocks of coupling the apparatus 101 to circuitry 503 and any other suitable components.

In some examples once the apparatus 101 has been formed the apparatus 101 may be coupled to one or more additional components to provide a wearable electronic device 601.

For example, the apparatus 101 may be secured to a strap 609 or other attachment means 603 to enable the apparatus 101 to be worn by a subject.

FIG. 9 illustrates an example integrated optoelectronic circuit 901 which may be used in the optical coherence tomography system 103 in some examples of the disclosure.

The integrated optoelectronic circuit 901 may be formed from a layer of silicon dioxide or from any other suitable material.

In the example of FIG. 9 the integrated optoelectronic circuit 901 comprises an interferometer 903, a light source 905 and at least one detector 909.

In the example of FIG. 9 the interferometer 903 comprises an input light guide 911, a beam splitter 913, a sample line light guide 915, a delay line light guide 917 and an output light guide 919. In the example of FIG. 2 the interferometer 903 also comprises a reflective mirror 907.

The input light guide 911 comprises means for receiving an input beam of light and propagating the input beam of light to the beam splitter 913. The input light guide 911 may be configured to be coupled to the light source 905. The light source 905 may comprise a coherent light source such as a laser or any other suitable light source 905.

In the example of FIG. 9 the light source 905 is provided as part of the integrated optoelectronic circuit 901. In other examples the light source 905 could be provided as a separate component to the integrated optoelectronic circuit 901.

The beam splitter 913 is configured to split the input beam of light into two components. A first component beam of light is directed down the sample line light guide 915 and a second component beam of light is directed down the delay line light guide 917. In the example of FIG. 9 the beam splitter 913 is a 50/50 beam splitter so that the first component beam of light and the second component beam of light are equal, for example in intensity. In other examples other types of the beam splitter may be used so that the component beams of light have different relative intensities.

The sample line light guide 915 comprises means for receiving the first component beam of light and propagating the first component beam of light to a sample 107. The sample 107 is not shown in FIG. 9. The sample 107 could comprise any suitable object. The sample 107 could comprise biological tissue of a subject. In some examples the sample 107 could comprise a subject's retina, teeth, skin or any other suitable body part. The sample line light guide 913 is configured so that light reflected from the sample 107 is propagated back towards the beam splitter 913 as a first reflected beam of light.

In the example interferometer 903 of FIG. 2 the delay line light guide 917 comprises means for receiving the second component beam of light and propagating the second component beam of light to a reflective mirror 907. The delay line light guide 917 is configured so that light reflected from the reflective mirror 907 is propagated back towards the beam splitter 913 as a second reflected beam of light.

The first reflected beam of light and the second reflected beam of light combine to provide an output beam of light. The output light guide 919 is configured to propagate the output beam of light out of the interferometer 903 and towards the detector 909.

In the example of FIG. 9 the detector 909 is provided as part of the integrated optoelectronic circuit 901. In other examples the detector 909 could be provided as a separate component to the integrated optoelectronic circuit 901.

In the example of FIG. 9 the detector 909 comprises a diode such as a photodiode. Other types of detector 909 may be used in other examples of the disclosure.

The electrical output of the detector 909 comprises information about the light reflected from the sample 107. This can be processed to generate a three dimensional image of the sample.

In the example of FIG. 9 the example integrated optoelectronic circuit 901 has a largest dimension of 10 mm or less. In the example of FIG. 9 the example integrated optoelectronic circuit 901 has a length of 10 mm or less and a width of 5 mm or less. Other sizes of the integrated optoelectronic circuit 901 could be used in other examples of the disclosure. The size of the integrated optoelectronic circuit 901 may be such that it enables the integrated optoelectronic circuit 901 and the apparatus 101 to be provided within a wearable device 601.

Examples of the disclosure provide for an apparatus 101 that can be used within wearable electronic devices 601 to enable the wearable electronic device 601 to be used for optical coherence tomography. As apparatus 101 can be provided within a wearable electronic device 601 this may enable the apparatus 101 to be used to obtain information about the subject at different times and/or over an extended time period. The extended time period could be hours, days, weeks or even longer.

In this description the term "coupled" means operationally coupled. Any number of intervening components may be provided between coupled components, including zero components.

The term "comprise" is used in this document with an inclusive not an exclusive meaning.

That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. An apparatus comprising:
an optical coherence tomography apparatus;
an optical arrangement wherein the optical arrangement comprises at least one lens configured to shape a beam of light from the optical coherence tomography apparatus and at least one mirror positioned so that light from the lens is incident on the at least one mirror and wherein the at least one mirror is configured to move in at least one direction relative to the optical coherence tomography apparatus to tuneably focus the light from the lens; and
an integrated optoelectronic circuit associated with the optical coherence tomography apparatus and comprising at least an interferometer configured for optical coherence tomography, the interferometer comprising a sample line light guide, a delay line light guide, and an output light guide;
wherein the optical coherence tomography apparatus is associated with circuitry configured to obtain an output from the optical coherence tomography apparatus and to provide image data;
wherein the at least one mirror is provided on a substrate and the substrate is provided at an incline of 45 degrees relative to the optical coherence tomography apparatus.

2. An apparatus as claimed in claim 1 further comprising a substrate wherein the optical arrangement and the optical coherence tomography apparatus are, at least in part, mounted on a substrate.

3. An apparatus as claimed in claim 1 wherein the at least one mirror comprises a micro-electromechanical mirror.

4. An apparatus as claimed in claim 1 wherein the optical arrangement comprises a first mirror configured to move in a first direction and also a second direction wherein the first direction is different to the second direction.

5. An apparatus as claimed in claim 4 wherein the second direction is perpendicular to the first direction.

6. An apparatus as claimed in claim 1 wherein the optical arrangement comprises a first mirror configured to move in a first direction and a second mirror configured to move in a second direction wherein the first direction is different to the second direction.

7. An apparatus as claimed in claim 1 wherein the at least one mirror is provided on a substrate and the mirror is provided at an incline relative to the substrate.

8. An apparatus as claimed in claim 1 wherein the lens comprises at least one spherical lens.

9. An optical arrangement comprising:
at least one lens configured to shape a beam of light from an optical coherence tomography apparatus associated with an integrated optoelectronic; and
at least one mirror positioned so that light from the lens is incident on the at least one mirror and wherein the at least one mirror is configured to move in at least one direction relative to the optical coherence tomography apparatus to tuneably focus the light from the lens;
wherein the integrated optoelectronic circuit comprises at least an interferometer configured for optical coherence tomography, the interferometer comprising a sample line light guide, a delay line light guide, and an output light guide;
wherein the optical coherence tomography apparatus is associated with circuitry configured to obtain an output from the optical coherence tomography apparatus and to provide image data;
wherein the at least one mirror is provided on a substrate and the substrate is provided at an incline of 45 degrees relative to the optical coherence tomography apparatus.

10. A wearable electronic apparatus comprising:
an optical coherence tomography apparatus comprising an integrated optoelectronic circuit, wherein the integrated optoelectronic circuit comprises at least an interferometer configured for optical coherence tomography, the interferometer comprising a sample line light guide, a delay line light guide, and an output light guide;
an optical arrangement wherein the optical arrangement comprises at least one lens configured to shape a beam of light from the optical coherence tomography apparatus and at least one mirror positioned so that light from the lens is incident on the at least one mirror and wherein the at least one mirror is configured to move in at least one direction relative to the optical coherence tomography apparatus to tuneably focus the light from the lens; and
an attachment configured to attach the optical coherence tomography apparatus to a subject;
wherein the optical coherence tomography apparatus is associated with circuitry configured to obtain an output and configured to provide image data;
wherein the at least one mirror is provided on a substrate and the substrate is provided at an incline of 45 degrees relative to the optical coherence tomography apparatus.

11. A wearable electronic apparatus as claimed in claim 10 wherein the attachment configured to attach the optical coherence tomography apparatus to a subject comprises a strap.

12. A wearable electronic apparatus as claimed in claim 10 wherein the optical arrangement and the optical coherence tomography apparatus are, at least in part, mounted on the substrate.

13. A wearable electronic apparatus as claimed in claim 10 wherein the at least one mirror comprises a micro-electromechanical mirror.

14. A wearable electronic apparatus as claimed in claim 10 wherein the optical arrangement comprises a first mirror configured to move in a first direction and also a second direction wherein the first direction is different to the second direction.

15. A wearable electronic apparatus as claimed in claim 10 wherein the optical arrangement comprises a first mirror configured to move in a first direction and a second mirror configured to move in a second direction wherein the first direction is different to the second direction.

16. A wearable electronic apparatus as claimed in claim 15 wherein the second direction is perpendicular to the first direction.

\* \* \* \* \*